(12) United States Patent
Reinmann et al.

(10) Patent No.: US 7,517,336 B2
(45) Date of Patent: Apr. 14, 2009

(54) MEMBRANE, MEMBRANE-CANNULA COMBINATION, AND CONNECTING DEVICE

(75) Inventors: Andreas Reinmann, Luterbach (CH); Marcel Hunn, Langenthal (CH)

(73) Assignee: Disetronic Licensing AG, Burgdorf (CH)

( * ) Notice: Subject to any disclaimer, the term of this patent is extended or adjusted under 35 U.S.C. 154(b) by 460 days.

(21) Appl. No.: 10/789,943

(22) Filed: Feb. 27, 2004

(65) Prior Publication Data
US 2004/0236274 A1 Nov. 25, 2004

Related U.S. Application Data

(63) Continuation of application No. PCT/CH02/00460, filed on Aug. 23, 2002.

(30) Foreign Application Priority Data

| Aug. 31, 2001 | (DE) | ................................ 101 42 637 |
| Sep. 6, 2001 | (DE) | ................................ 101 43 820 |
| Sep. 6, 2001 | (DE) | ............................ 201 14 795 U |

(51) Int. Cl.
*A61M 5/178* (2006.01)
*F16L 37/28* (2006.01)

(52) U.S. Cl. ............................... 604/167.03; 251/149.1

(58) Field of Classification Search ................... 604/86, 604/88, 30, 34, 246, 244, 250, 167.01–167.05, 604/256, 537; 251/149.1
See application file for complete search history.

(56) References Cited

U.S. PATENT DOCUMENTS

| 5,354,275 | A | | 10/1994 | Behnke et al. |
| 5,405,331 | A | | 4/1995 | Behnke et al. |
| 5,520,641 | A | * | 5/1996 | Behnke et al. ................. 604/86 |
| 6,210,377 | B1 | * | 4/2001 | Ouchi ......................... 604/264 |
| 2001/0041872 | A1 | * | 11/2001 | Paul, Jr. .................. 604/167.04 |

FOREIGN PATENT DOCUMENTS

WO WO 99/34754 7/1999

* cited by examiner

*Primary Examiner*—Matthew F Desanto
(74) *Attorney, Agent, or Firm*—Dorsey & Whitney LLP

(57) ABSTRACT

A membrane with at least one passage extending through an elastic material of the membrane, wherein when a cannula is inserted in the passage, the passage is expanded and the elastic material presses against the cannula and surrounds the cannula in a seal, wherein the membrane can be compressed relative to the passage, and wherein, in one embodiment, the passage exhibits a cross-sectional area having a long main axis and a short main axis perpendicular to the long main axis. The invention encompasses a membrane-cannula combination for biological and medical uses, and a membrane-connecting device combination for connecting a fluid guide and a catheter.

19 Claims, 3 Drawing Sheets

MEMBRANE, MEMBRANE-CANNULA COMBINATION, AND CONNECTING DEVICE

CROSS-REFERENCE TO RELATED APPLICATION(S)

This application is a continuation of International Application No. PCT/CH02/00460, filed Aug. 23, 2002, which claims priority to German Application No. 101 42 637.0, filed Aug. 31, 2001, German Application No. 201 14 795.5, filed Sep. 6, 2001, and German Application No. 101 43 820.6, filed on Sep. 6, 2001, the contents of which are incorporated in their entirety by reference.

BACKGROUND

The present invention relates to medical and biotechnological devices and methods and, more particularly, to a membrane, a membrane-cannula combination and a connecting device for medical and biotechnological applications or uses, including uses in which sterility is involved. In some preferred embodiments, the invention is used in infusion means and methods, dialysis, perfusion or rinsing means and methods, and measuring means and methods.

In medicinal technology, in particular in human medicine, fluid guiding conduits—for example, catheters—have to be connected to each other, typically in sealed and sterile condition. Such a connection is particularly critical in the case of a body access device which is permanently implanted percutaneously or subcutaneously in a biological tissue, in particular in the human body. If a connection can only be established after the device has been implanted, or if it is to be possible to detach and re-establish the connection, then the demands on the sterile seal of a connecting point between the fluid guiding conduits increase.

Body access devices such as those to which the invention relates are known, for example, from EP 0 867 197, EP 0 867 196 and EP 0 867 198. In these devices, a sterile seal of a connection which can be repeatedly detached and established, between two fluid conduits within a percutaneously implanted port body, can be established by means of a membrane made of an elastic material. The membrane is arranged in the port body and comprises a self-closing passage. One of the fluid conduits is an implanted catheter guided into the port body. The other fluid conduit to be connected is formed by a rigid, thin cannula which can be inserted into the passage. The membrane surrounds an outer surface of the cannula inserted into the passage, forming a seal all around. The membrane creates a sealed connection in the port body between the implanted catheter and the cannula guided into the port body from outside the body.

SUMMARY

It is an object of the invention to improve the seal between a membrane and a cannula inserted into the membrane.

In one embodiment, the present invention relates to a membrane for biological applications, in particular for medicinal technological applications, and within medicinal technology, preferably for applications in human medicine. The membrane is, however, equally suitable for uses in biology in general, for example in veterinary medicine, but also outside medicine.

In one embodiment, the present invention comprises a membrane with at least one passage extending through an elastic material of the membrane, wherein when a cannula is inserted in the passage, the passage is expanded and the elastic material presses against the cannula and surrounds the cannula in a seal. In one embodiment, the membrane can be compressed at an angle relative to the passage and, in one embodiment, the passage exhibits a cross-sectional area having a long main axis and a short main axis perpendicular to the long main axis. In some embodiments, the present invention comprises a membrane-cannula combination for biological and medical uses and, in some embodiments, a membrane-connecting device combination for connecting a fluid guide and a catheter.

In one embodiment, the membrane comprises an elastic material or is formed completely from an elastic material as a membrane body. The elastic material can be any suitable material, for example, silicone or latex. A combination of a number of different elastic materials can also be used. At least one passage or channel for a cannula, and in some preferred embodiments exactly one passage, extends through the membrane. The membrane is conditioned or installed in a casing in such a way that the passage is expanded when a cannula having a correspondingly sized cross-section is inserted into the passage. In the event of a radial expansion of the passage, the elastic material of the membrane elastically presses against a surface of the cannula and elastically encompasses the surface of the cannula in a seal, such that—in a preferred use in medicinal technology in a fluid guiding system—the seal ensures the sterility required.

In accordance with one embodiment of the present invention, the membrane can be compressed perpendicularly relative to the passage. If the membrane is advantageously tightly enclosed over its entire surface, the elastic expansion of the passage can be ensured due to the compressibility. In some preferred embodiments, the membrane is tightly enclosed in a casing in such a way that the membrane in the enclosure is already compressed perpendicularly to the passage before a cannula is inserted into the passage. In this state, the passage is particularly preferably closed by the compression forces. This closure is preferably also sufficiently sealed to ensure the sterility required for medical applications.

In some preferred embodiments, the membrane's compressibility is achieved by forming at least one hollow space in the elastic material of the membrane next to the passage, into which space the membrane can be deformed when compressed. In some preferred exemplary embodiments, the membrane comprises a number of hollow spaces in the elastic material of the membrane next to the passage. Said number of hollow spaces preferably extend through the membrane next to the passage. In some embodiments, they particularly preferably run parallel to the passage. Instead of by forming or shaping measures, or in combination with forming, the hollow spaces can also be formed by the pores of an elastic, porous, but overall non-permeable material, i.e. by means of a porous material whose pores are closed. Such a porous material can also surround an elastic, non-porous material, and the passage would extend through the non-porous material. Ultimately, the hollow spaces or the at least one hollow space also does not necessarily have to be formed within the elastic material, although in some embodiments this is preferred. The hollow spaces or the at least one hollow space can be formed as recesses or a recess on an outer circumference of the elastic material.

By forming at least one hollow space next to the passage, the passage can in principle exhibit any cross-sectional shape. Thus, when the membrane is not stressed and is free of exterior forces, the cross-section of the passage can be narrower than an outer cross-section of the cannula, along the entire length of the passage.

In a preferred embodiment, the passage exhibits an elongated cross-sectional area with a long main axis and a short main axis perpendicular to the long main axis, when the membrane is not stressed. When the membrane is not stressed, the passage can be formed by a slit. In this case, the length of the short main axis is zero. In some preferred embodiments, however, the passage exhibits a cross-sectional area other than zero when the membrane is not stressed. The long main axis and the short main axis are the long side and the short side of the smallest rectangle which surrounds the cross-sectional area of the passage. The cannula to be inserted usually exhibits a circular cross-section. The length of the long main axis of the cross-section is preferably larger than an average cannula diameter. In this way, a hollow space into which the elastic material of the membrane can yield can be formed by the passage. A hollow space formed between the cannula and the elastic material can alone form the at least one hollow space by which compressibility is obtained.

The cross-sectional shape in accordance with the invention improves the seal of the passage closure by radially compressing the membrane, both before and after inserting the cannula.

In some embodiments, the elongated cross-section, i.e. the elongated cross-sectional area, of the passage is preferably oval. The cross-section can for example be elliptical. In the sense of the invention, an oval is also understood as a cross-section comprising straight sections between rounded regions. In some embodiments, a cross-section with a constantly curved circumference is preferred.

If the passage exhibits an elongated cross-section and a number of hollow spaces are additionally arranged next to the passage, as corresponds to some particularly preferred embodiments, then the hollow spaces are advantageously arranged in the cross-sectional plane, axially symmetrical with respect to at least one of the main axes, preferably the long main axis, of the passage cross-section. In some preferred embodiments, they are arranged axially symmetrical with respect to both main axes. If the passage is formed and the hollow spaces arranged in this way, the elastic material of the membrane is deformed substantially evenly into the hollow spaces next to the passage when the passage is expanded, and the elastic material abuts the inserted cannula substantially evenly. With respect to a longitudinal axis of the membrane, perpendicular to the cross-section with the two main axes, the hollow spaces are preferably not arranged rotationally symmetrically about this longitudinal axis. In some embodiments, the hollow spaces are preferably concentrated towards the short main axis, and hollow spaces are particularly preferably not provided on the long main axis and preferably also not in the immediate vicinity of the long main axis.

In some embodiments, the cross-sectional area of the passage is preferably not edged at its narrow ends, at least not sharp-edged, but rounded, preferably evenly rounded. Using this shape of the cross-sectional area, it is possible to particularly well ensure that a thick cannula with an outer diameter of, for example, 1 mm can be inserted into the passage without being damaged, and it is nonetheless ensured that the material of the membrane evenly abuts the surface of the cannula, forming an elastic seal.

In some embodiments, the membrane is preferably used to convey a biological or biologically active fluid, and is particularly preferably used for a connecting device for establishing a connection between two fluid conduits. A biological fluid can, for example, be a human or animal body fluid. A biologically active fluid can, for example, be formed by a medically active substance or can contain such a substance.

In a preferred embodiment, the connecting device is a body access device comprising a port body which can be percutaneously or subcutaneously implanted. A port body which can be percutaneously implanted protrudes from the surface of the skin and protrudes into the skin and preferably under the skin into the body tissue. A port body which can be subcutaneously implanted is implanted under the skin and usually comprises a membrane placed towards the skin which can be pierced by means of a needle injected under the skin, for the purpose of establishing a fluid connection.

In a particularly preferred embodiment of the port body or also of a different connecting device, a curved catheter section can be protected by forming a casing opening for the catheter in a recess of a casing surface and accommodating the catheter in the recess at the connection to the casing opening. It is common with implanted catheters for the catheter section directly at the connection to the casing opening to curve or bend, since in order to reduce the danger of infection at the end of the catheter, the catheters are guided directly under the skin for a certain distance and the skin is tunneled, so to speak. In this way, for example when used within the framework of an intravenous injection or infusion, the implanted catheter may be guided for several hundred millimeters into or in a vein. As a consequence of the bend in the catheter directly at the implanted port body, there exists in the region of the bend in the catheter an increased danger of blockage. The danger of blockage is significantly reduced by means of the recess and the protection for the catheter which it forms. In this embodiment, the casing protects the bent region of the catheter against mechanical pressure forces from without.

In some particularly preferred embodiments, the recess gradually tapers towards the casing opening at least from one side, and is swelled outwards. Forming the recess in this way is advantageous when using a flexible catheter, since bending by the catheter can be reliably avoided. The catheter can, however, also be formed by a rigid pipe section in its bent region.

Although arranging the casing opening for the catheter in a recess is particularly advantageous in conjunction with the membrane and membrane-cannula combination in accordance with the present invention, such an embodiment of a casing of a connecting device—preferably a body access device—can also be advantageously provided in conjunction with conventional membranes and membrane-cannula combinations.

Another particularity of embodiments of a body access device in accordance with the present invention is the tilt-resistant support of the fluid guiding means directly at a port body or, preferably, at a casing for the membrane which may be fastened in the port body. This refers to the mechanical connection between the fluid guiding means and the port body, which does not necessarily relate exclusively to the membrane or membrane-cannula combination in accordance with the present invention.

DETAILED DESCRIPTION

Figure 1:
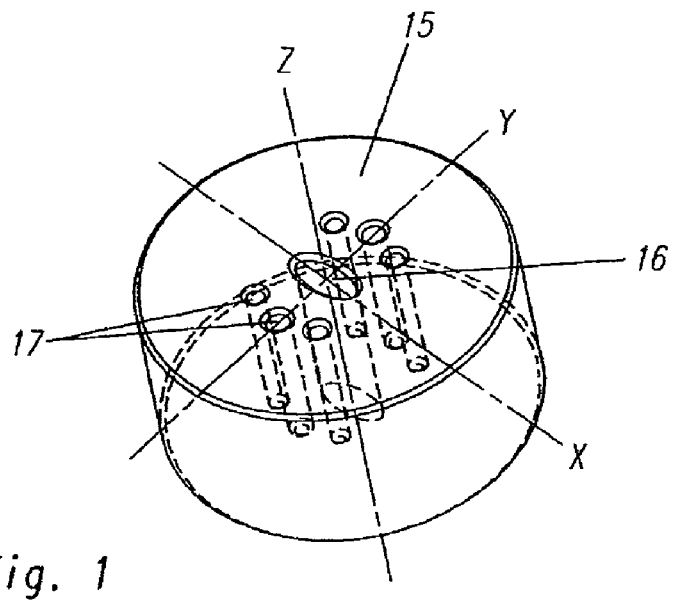
FIG. 1 depicts a membrane in accordance with one embodiment of the present invention.

FIG. 1 shows a membrane 15 formed as a circular-cylindrical body made of a suitable, generally homogenous, elastic material, for example silicone or latex. A passage 16 extends, concentrically with respect to a central longitudinal axis Z, through the membrane 15. The passage 16 is linearly cylindrical and exhibits a cross-sectional area which remains generally constant in size and shape over its entire length. The cross-sectional area of the passage 16 is elongated, i.e. it exhibits a long main axis X and a short main axis Y which point generally perpendicularly to the longitudinal axis Z of the membrane 15. In the exemplary embodiment, the cross-sectional area is oval, e.g. elliptical.

Spaced from the central passage 16, a number of hollow spaces 17 are formed in the membrane 15. The hollow spaces 17 are formed by simple, linearly cylindrical passages which extend through the membrane 15 between the two facing areas of the membrane 15. The hollow spaces 17 are arranged generally axially symmetrically with respect to the long main axis X. They are furthermore also arranged generally axially symmetrically with respect to the short main axis Y, wherein a build up of hollow spaces 17 arises towards the short main axis Y. There are no hollow spaces provided in the immediate vicinity of the long main axis X and in particular on the long main axis X. The hollow spaces 17 run parallel to the longitudinal axis Z. The hollow spaces 17 are arranged along a line which runs around the longitudinal axis Z, spaced approximately or, in some preferred embodiments, exactly parallel to the rim of the passage 16.

Figure 1A:
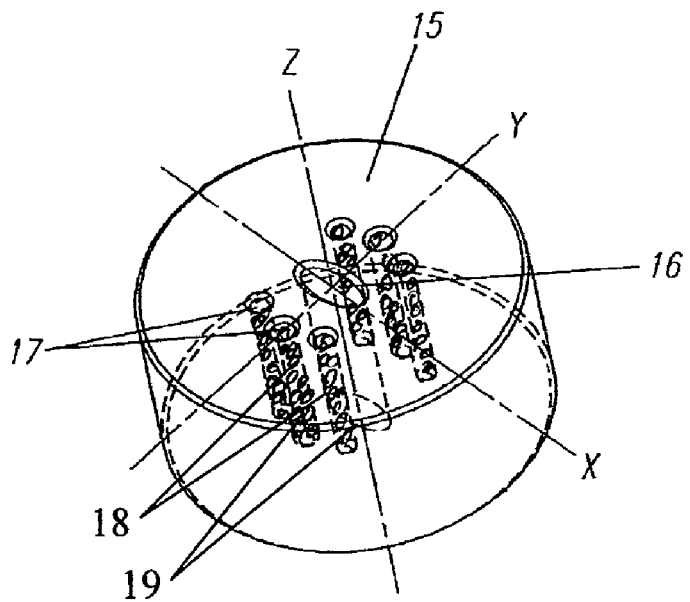
FIG. 1a depicts a membrane in accordance with another embodiment of the present invention.
Figure 1B:
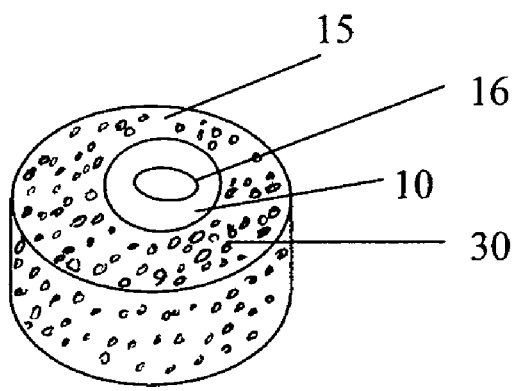
FIG. 1b depicts a membrane in accordance with yet another embodiment of the present invention.

FIG. 1a shows a membrance 15 with passage 16 similar to that depicted in FIG. 1, except the cylindrical passages 17 which extend through the membrane 15 between the two facing areas of the membrane 15 include one or more hollow spaces formed by the pores 18 of an elastic, porous, but overall non-permeable material 19, i.e. by means of a porous material whose pores are closed. FIG. 1b shows a membrance 15 with passage 16 extending through a non-porous portion 10 of the membrane 15. A porous material 30 surrounds the elastic, non-porous material, and the porous material 30 provides at least one hollow space in the elastic material of the membrane next to the passage, into which space the membrance can be deformed when compressed.

Figure 2:
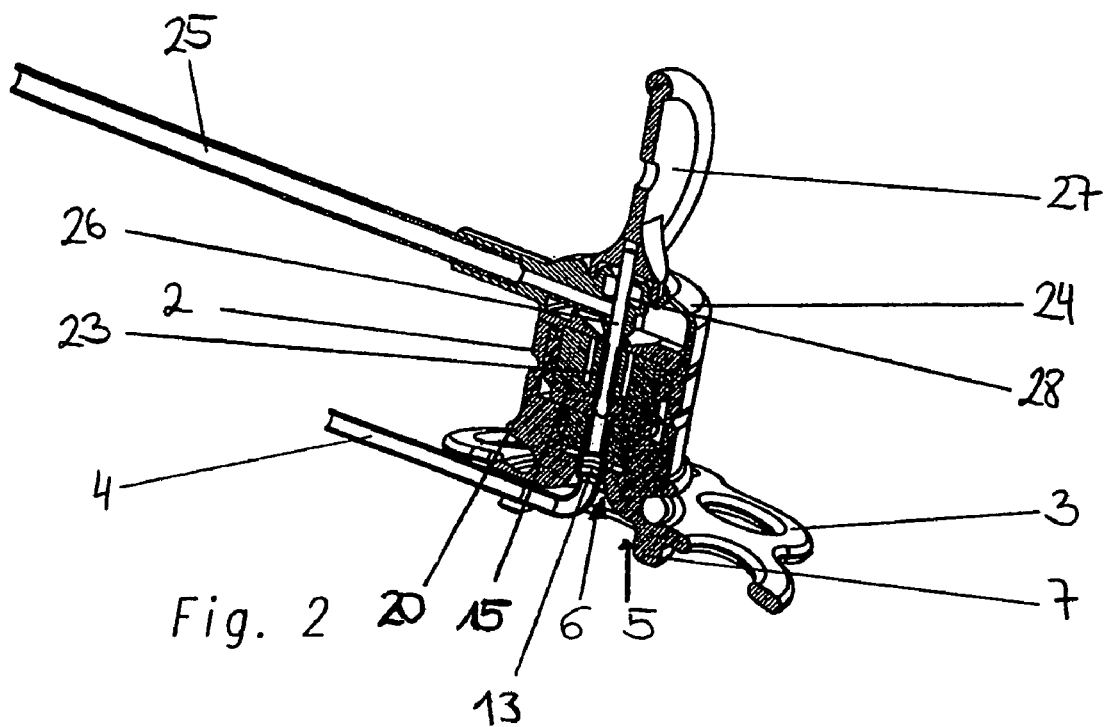
FIG. 2 depicts a first embodiment of a connecting device in accordance with the invention, in a longitudinal section.

FIG. 2 shows an exemplary installation for the membrane 15 using the example of a connecting device via which two catheters 4 and 25 are connected to each other. The membrane 15 is inserted into a hollow-cylindrical, cup-shaped membrane casing 20. The membrane casing 20 tightly encloses the membrane 15 on its surface area, i.e. the membrane 15 is radially supported by the membrane casing 20 over its entire outer surface area. The membrane 15 can be force-fitted in the membrane casing 20 and thereby pre-compressed. On its upper side, the membrane casing 20 comprises a base with a central passage opening.

A cannula 23 is inserted through a base of the membrane casing 20 and protrudes through the passage 16 of the membrane 15. The cannula 23 is sufficiently rigid to form a flow cross-section for conveying a fluid, even under the radial pressure of the elastic material of the compressed membrane 15. The membrane 15 is elastically compressed into the hollow spaces 17 of the membrane 15 between the enclosing cylinder wall of the membrane casing 20 and the cannula 23 guided through the passage 16. Although, in some embodiments it is preferred if the hollow spaces 17 are closed in a seal by compressing the membrane 15, such a sealed closure of the hollow spaces 17 is not necessarily required if fluid can be prevented from passing through the hollow spaces 17 in other ways. In the exemplary embodiment of the connecting device, the membrane 15 presses via its two facing areas against walls of the connecting device, namely against the base of the membrane casing 20 and against a facing area of the connecting device opposite the base. A sealed closure of the hollow spaces 17 already occurs against these two facing areas.

In some embodiments, the cannula 23 is preferably linearly cylindrical with a circular cross-section. The outer diameter of the cannula 23 is larger than the diameter of the membrane 15 measured in the direction of the short main axis Y, wherein this specification relates to FIG. 1 in which the membrane 1 is not stressed and is free of exterior forces. In the membrane-cannula combination formed by the membrane 15 and the cannula 23, the membrane 15 can be elastically compressed solely by expanding the passage 16 due to the inserted cannula 23. If the membrane 15 is already in the membrane casing 20 pre-compressed, in one preferred embodiment, radially pre-compressed, the diameter of the cannula 23 can also be smaller than the diameter of the passage 16 measured in the direction of the short main axis Y. The membrane 15 is in this case merely compressed even more, in addition to its pre-compression. The diameter of the passage 16 measured in the direction of the long main axis X is larger than the outer diameter of the cannula 23.

The connecting device in FIG. 2 is a body access device. Body access devices represent preferred exemplary embodiments of a connecting device in accordance with the invention. It is not, however, absolutely necessarily for connecting devices in accordance with the invention to be formed by body access devices. In the following, use of the term body access device is therefore not intended to exclude other connecting devices in which the invention may be used.

Figure 3:
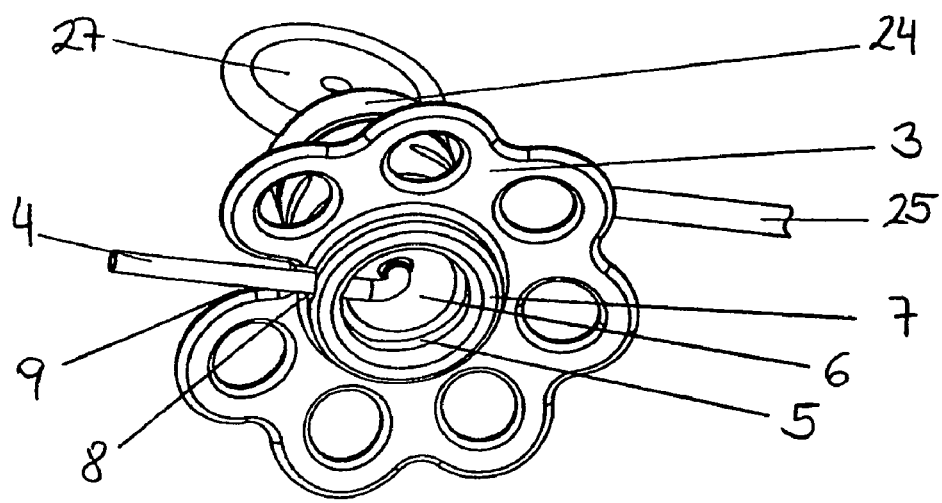
FIG. 3 depicts the connecting device of FIG. 2.

FIG. 3 shows the body access device of FIG. 2, in a view onto an underside.

Figure 5:
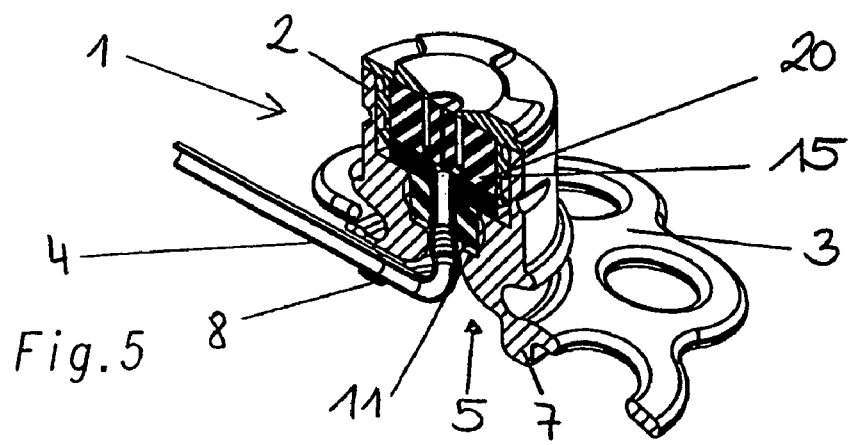
FIG. 5 depicts the port body of FIG. 4 with the membrane of FIG. 1, in longitudinal section.
Figure 6:
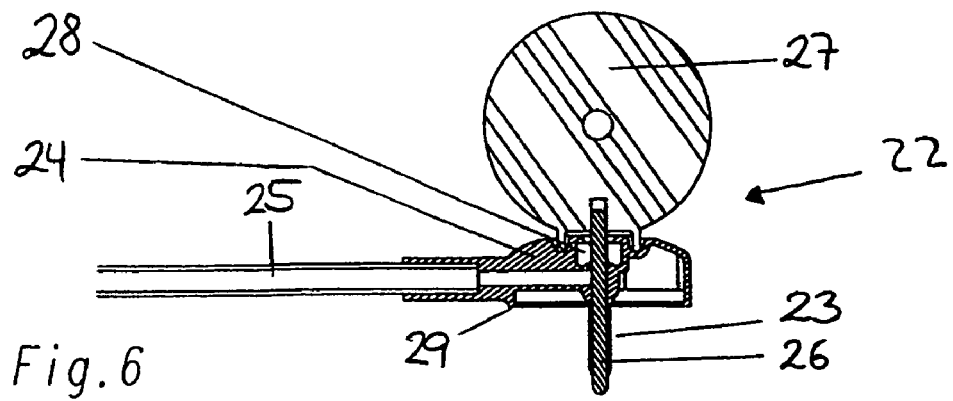
FIG. 6 depicts the fluid guiding means of FIGS. 2 and 3, in longitudinal section.

The body access device is formed by a port body 1 and a fluid guiding means 22, which are shown individually in FIGS. 5 and 6. FIGS. 2 and 3 show the port body 1 and the fluid guiding means 22 connected, wherein a sealed connection is established between the catheter 4 and the catheter 25 by the device and in particular by the membrane 15-cannula 23 combination.

The port body 1 is provided for percutaneous implantation in the human body. A planar anchoring body 3, curved like an umbrella and from which a hollow-cylindrical casing 2 protrudes generally perpendicularly, serves to anchor the device in cellular tissue, in particular under the skin. The casing 2 is open on a facing side facing away from the anchoring body 3. The casing 2 and the anchoring body 3 are injection-molded in one piece from a bio-compatible plastic material.

The catheter 4 is implanted in the human body. One end of the catheter 4 protrudes into the casing 2 through an opening formed in the region of a base of the casing 2. The base is formed by an annular stay 11 (FIG. 5) at the level of the anchoring body 3 and/or in the region of the transition from the anchoring body 3 to the casing 2.

Figure 4:
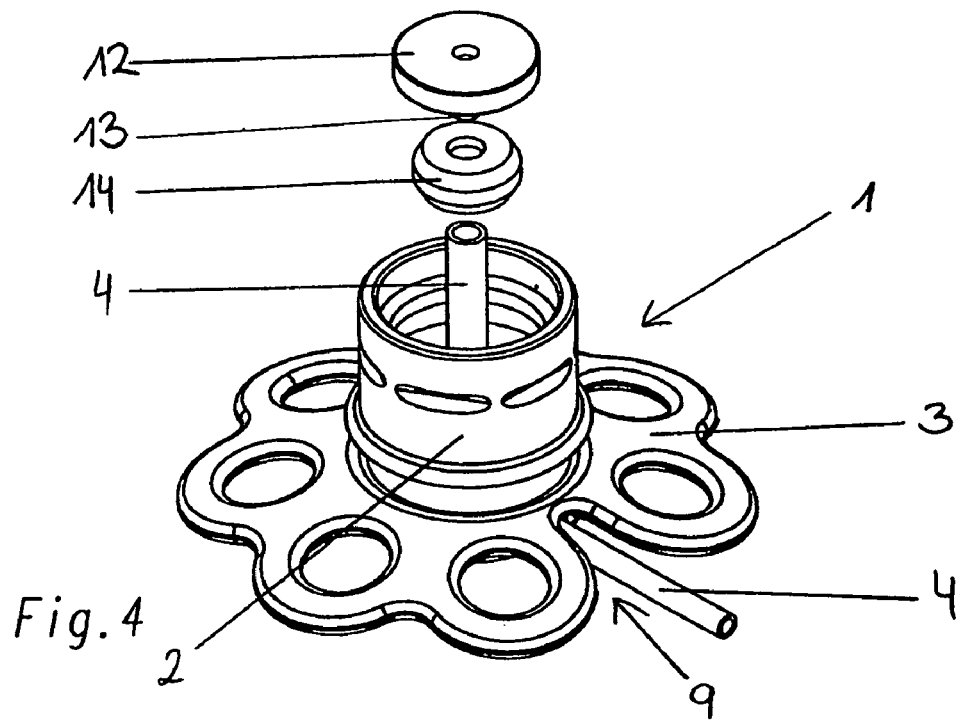
FIG. 4 depicts the port body of the connecting device of FIGS. 2 and 3.

FIG. 4 shows how the catheter 4 is fastened in the casing 2. The end of the catheter 4 is inserted into the casing 2 through the opening. The end of the catheter 4 is then inserted into a clamping ring 14, and a connecting piece 13—which projects from a disc-shaped supporting sleeve 12 and comprises bulged rings on its outer surface—is force-fitted into the end of the catheter 4 surrounded by the clamping ring 14. When assembled, as shown in FIG. 5, the clamping ring 14 is accommodated in a region of the casing 2 connected to the casing opening. The casing 2 is radially widened over the clamping ring 14. The supporting sleeve 12 rests on an annular collar formed by the widening in the casing 2.

Once the catheter 4 has thus been secured against slipping out through the opening formed on the underside of the casing 2, the membrane casing 20 with the membrane 15 accommodated in it is inserted into the casing 2 in such a way that the membrane 15 presses via its facing area against an upper side of the supporting sleeve 12 and seals a passage extending through the supporting sleeve 12 and its connecting piece 13 into the catheter 4, all around. The passage 16 of the membrane 15 is flush with the end of the catheter 4. In the course of insertion, the casing 2 and the membrane casing 20 are connected to each other in a positive lock. To this end, they comprise suitable connecting structures or latching means which latch to each other. The latching means of the casing 2 is formed by an annular rib protruding radially from the inner surface of the casing 2, and the outer surface of the membrane casing 20 is provided with a corresponding annular groove into which the annular stay of the casing 2 latches when the membrane casing 20 is inserted. Establishing the latching connection generates an easily audible click. FIG. 5 shows the port body 1 in this state, i.e. once the latching connection between the port body casing 2 and the membrane casing 20 has been established.

As shown in FIG. 6, a fluid guiding means 22 which may be connected in a positive lock to the port body 1 of FIG. 5 comprises a cannula casing 24 from which the cannula 23 protrudes and into which the catheter 25 is guided, generally perpendicular to the cannula 23. The catheter 25 is sealed in a lateral connecting piece of the cannula casing 24. A fluid channel which extends the catheter 25 in the cannula casing 24 leads into the cannula 23.

For inserting the cannula 23 into the passage 16 of the membrane 15, a connecting pin 26 protrudes through the cannula 23. In some embodiments, the connecting pin 26 solely serves the purpose of ensuring that the cannula 23 is inserted without damaging the membrane 15. To facilitate this, a front end of the connecting pin 26 is formed rounded. The front end of the connecting pin 26 protrudes a little way out of the cannula 23. In conjunction with the connecting pin 26, a softly rounded front end is obtained for the cannula 23. In this way, the front end of the cannula 23 can even be sharp-edged.

The cannula 23 extends in the cannula casing 24 beyond the fluid channel for the catheter 25, as viewed from its front open end. A septum 28 is arranged in the extended region. The connecting pin 26 is inserted into the cannula 23 through the septum 28. The septum 28 ensures that the cannula 23 is hermetically sealed when the connecting pin 26 is inserted and also after the connecting pin 26 has been removed.

On an underside which the cannula 23 protrudes beyond, the cannula casing 24 comprises latching means 29 in the form of latching ribs which protrude radially inwards from a circumferential, free rim of the cannula casing 24. In an upper region facing away from the anchoring body 3, the membrane casing 20 is provided with corresponding connecting or latching means in the form of notches which the latching means 29 of the cannula casing 24 latch into. When latched, the cannula casing 24 tightly embraces the upper opening rim of the membrane casing 20, thus obtaining a tilt-resistant guidance of the fluid guiding means 22 on the membrane casing 20 and therefore ultimately on the casing 2.

In order to establish the fluid connection between the catheter 25 and the catheter 4 after the port body 1 and the fluid guiding means 22 have been latched, the connecting pin 26 is removed from the cannula 23. Removing the connecting pin 26 is facilitated by forming a connecting grip 27 on an end of the connecting pin 26 protruding from the cannula casing 24.

In one embodiment, one particularity of the body access device is that of arranging the opening for the catheter 4 in a recess 5 on the underside of the port body 1. The recess 5 is pocket-shaped and is enclosed by a limiting ring 7 which protrudes from the anchoring body 3 on the underside of the port body 1, roughly in the extension of the cylindrical casing 2. Within the limiting ring 7, the recess 5 tapers, in the shape of a funnel, into the casing opening formed in the annular stay 11.

In the course of the taper, the recess 5 is softly rounded and swelled, up to the opening rim of the annular stay 11 which leads into the casing 2, thus obtaining a trumpet-shaped funnel. From the casing opening, the catheter 4 exhibits a curvature—adapted to the shape of the funnel—of about 90°. In the recess 5, the funnel exhibits a depth which, measured perpendicularly to the opening cross-section, is sufficiently large to deflect the catheter 4 by the required angle, preferably 90°, at least without producing kinks.

Directly connected to its curved or deflected region, the catheter 4 is guided by a guiding passage 8 formed in the limiting ring 7. The guiding passage 8 can be formed by a notch, open towards the underside, in the limiting ring 7. In some preferred embodiments, it is formed—as in the exemplary embodiment—by a hole in the limiting ring 7, through which the catheter 4 is guided. In this way, the catheter 4 is simultaneously also fixed on the underside of the body access device.

Viewed in the extension of the guiding passage 8 from the casing opening for the catheter 4, the anchoring body 3 comprises a cavity 9 which extends from the outer circumference into the anchoring body 3 and thus interrupts the anchoring body 3 from the rim. In the region of the cavity 9, the catheter 4 is guided out of the region of the anchoring body 3. The cavity 9 ensures that the anchoring body 3 cannot press on the catheter 4 and thereby reduce the flow cross-section of the catheter 4 or even completely seal off the catheter 4. Furthermore, cavity 9 enables the catheter 4 to be guided particularly tightly on the port body 1.

In the foregoing description, embodiments of the present invention, including preferred embodiments, have been presented for the purpose of illustration and description. It is not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The inventions claimed is:

1. A membrane for biological applications, comprising an elastic material and at least one passage which extends through the elastic material, one of the at least one passage having an oval cross-section, and at least one cylindrical compressible space in the elastic material arranged parallel to the at least one passage, wherein an elastic, closed pore, non-permeable material is within the at least one cylindrical compressible space forming at least one hollow space in the membrane, and when said passage having the oval cross-section is expanded, which occurs when a cannula is inserted in the passage, said elastic material elastically presses against said cannula and surrounds the cannula in a seal, and the membrane can be compressed perpendicularly relative to the passage into the at least one hollow space.

2. The membrane as set forth in claim 1, wherein the at least one cylindrical compressible space is next to the passage.

3. The membrane as set forth in claim 2, wherein the at least one cylindrical compressible space extends through the elastic material next to the passage.

4. The membrane as set forth in claim 1, wherein a number of cylindrical compressible spaces are formed in the elastic material of the membrane and are generally axially symmetrical with respect to an axis of symmetry which extends in a cross- sectional plane of the passage.

5. The membrane as set forth in claim 4, wherein the cylindrical compressible spaces are not rotationally symmetrical with respect to a longitudinal axis of the membrane which is generally perpendicular to said cross-sectional plane of the passage.

6. A membrane for biological applications, comprising at least one passage which extends through an elastic material of said membrane, wherein when said passage is expanded, which occurs when a cannula is inserted into the passage, said material elastically presses against said cannula and surrounds the cannula in a seal, wherein the passage exhibits a cross-sectional area comprising a long main axis and a short main axis generally perpendicular to said long main axis, said long main axis and short main axis having a length greater than zero;
 wherein a number of cylindrical compressible spaces formed by an elastic, closed pore, non-permeable material within the at least one cylindrical compressible space forming at least one hollow space in the membrane, and said cylindrical compressible spaces are generally adjacent to the passage and are generally axially symmetrical with respect to an axis of symmetry which extends in a cross-sectional plane of the passage; and
 wherein the compressible spaces are generally axially symmetrical on both sides of the long main axis.

7. The membrane as set forth in claim 6, wherein the oval shaped cross-section area exhibits a circumference with a constant curvature.

8. A membrane-cannula combination for biological applications, said combination comprising:
 a) a cannula for conveying a fluid;
 b) a casing;
 c) and a membrane accommodated by said casing and comprising an elastic membrane material through which a passage having an oval shaped cross-section is formed, into which said cannula can be inserted, and a number of cylindrical compressible spaces comprising an elastic, closed pore, non-permeable material within the at least one cylindrical compressible space forming at least one hollow space in the membrane, the cylindrical compressible spaces are generally axially symmetrical with respect to an axis of symmetry which extends in a cross-sectional plane of the passage;
 d) wherein when said passage is expanded by inserting the cannula through the passage of said membrane, material presses against the compressible spaces and said casing, generally perpendicularly relative to the passage, and elastically presses against the inserted cannula such that the membrane material surrounds the cannula in a seal; wherein
 e) the passage and the cannula exhibit different cross-sectional shapes relative to each other before the cannula is inserted.

9. The membrane-cannula combination as set forth in claim 8, wherein the number of compressible spaces are next to the passage.

10. The membrane-cannula combination as set forth in claim 9, wherein the at least one compressible space extends through the elastic material next to the passage.

11. The membrane-cannula combination as set forth in claim 8, wherein the cylindrical compressible spaces are not rotationally symmetrical with respect to a longitudinal axis of the membrane.

12. A connecting device for connecting a fluid guiding means for a biological or biologically active fluid to a catheter, said connecting device comprising:
 a) a casing comprising an inlet for said catheter;
 b) a cannula which forms a front end of said fluid guiding means;
 c) and an elastic membrane comprising a passage having an oval cross-section into which said cannula can be inserted to establish the connection, and a number of cylindrical compressible spaces comprising elastic, closed pore, non-permeable material within the at least one cylindrical compressible space forming at least one hollow space in the membrane, the cylindrical compressible spaces are formed in the membrane and are generally axially symmetrical with respect to an axis of symmetry which extends in across-sectional plane of the passage;
 d) wherein said membrane is accommodated by said casing in such a way that a sealed connection is established between the catheter and the cannula by the membrane; wherein
 e) when the cannula is inserted in the passage, the passage is expanded, and said elastic membrane elastically presses against the compressible spaces and said cannula and surrounds the cannula in a seal, wherein the membrane can be compressed perpendicularly relative to the passage.

13. The connecting device as set forth in claim 12, wherein a casing inlet for the catheter is formed in a recess of a casing surface and said recess exhibits a sufficient size to accommodate a curved section of the catheter.

14. The connecting device as set forth in claim 13, wherein the recess gradually tapers towards the inlet.

15. The connecting device as set forth in claim 12, wherein said connecting device forms a body access device, the catheter can be implanted, and the casing is a port body which can be percutaneously or subcutaneously implanted.

16. A connecting device for connecting a fluid guiding means for a biological or biologically active fluid to a catheter, said connecting device comprising:
 a) a casing comprising an inlet for said catheter;
 b) a cannula which forms a front end of said fluid guiding means; an
 c) an elastic membrane comprising a passage having an oval cross-section into which said cannula can be inserted, to establish the connection; wherein
 d) said membrane is accommodated by said casing in such a way that a sealed connection is established between the catheter and the cannula by the membrane, and wherein the cross-sectional area of the passage comprises a long main axis and a short main axis generally perpendicular to said long main axis;

e) wherein a number of cylindrical compressible spaces comprising elastic, closed pore non-permeable material within the at least one cylindrical compressible space forming at least one hollow space in the membrane, the cylindrical compressible spaces of the membrane and are generally axially symmetrical with respect to an axis of symmetry which extends in a cross-sectional plane of the passage; and f) wherein the cylindrical compressible spaces are generally axially symmetrical on both sides of the long main axis.

17. The connecting device as set forth in claim 16, wherein the casing inlet for the catheter is formed in a recess of a casing surface and said recess exhibits a sufficient size to accommodate a curved section of the catheter.

18. The connecting device as set forth in claim 17, wherein the recess gradually tapers towards the inlet.

19. The connecting device as set forth in claim 16, wherein said connecting device forms a body access device, the catheter can be implanted, and the casing is a port body which can be percutaneously or subcutaneously implanted.

* * * * *